US00PP09259P

United States Patent [19]

Mantel

[11] Patent Number: Plant 9,259

[45] Date of Patent: Aug. 22, 1995

[54] LILIUM 'BALLERINA'

[76] Inventor: Homme Mantel, 15361 SE. Bluff Rd., P.O. Box 1314, Sandy, Oreg. 97009

[21] Appl. No.: 358,139

[22] Filed: Dec. 6, 1994

[51] Int. Cl.[6] ..... A01H 5/00

[52] U.S. Cl. ..... Plt./87.4

[58] Field of Search ..... Plt. 87.4

[56] References Cited

PUBLICATIONS

Leslie, A. C. "Ballerina" *The International Lily Register* 1982, The Royal Horticultural Society, p. 30.

*Primary Examiner*—James R. Feyrer

[57] ABSTRACT

A new variety of hybrid lily plant outfacing to semi-upfacing flowers of excellent form and long persistence, both on the plant and as cut-flowers. The new hybrid is particularly characterized by its elongate racemose inflorescence with occasional secondary buds, borne on slightly ascending pedicels, and by its many outfacing to semi-upfacing, non-fading, deep orange or orange-red flowers. This combination is completely new in the Asiatic hybrid divisions of lilies suited to forcing and to mass commercial cultivation. The variety is resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1989 in't Zandt, the Netherlands. The breeding efforts had as their objective the production of Asiatic hybrid lilies with an elongate inflorescence bearing many orange or red-orange flowers, suited to forcing into flower out of season, heretofore unknown in lily breeding art.

I achieved the desired objective by pollinating *Lilium* 'Matchless' (U.S. Plant Pat. No. 4,879) with a tall, deep red outfacing Asiatic unnamed seedling. This pollen parent was produced by me and never released; it was produced from 'Chinook' (unpatented)×'Burgundy' strain (unpatented). 'Chinook' was grown commercially in the United States and the Netherlands as a garden lily and cut-flower variety during the 1970's and 1980's; 'Burgundy' strain was grown commercially in the United States as a garden lily.

The flowers of my new lily are characterized by outfacing to semi-upfacing orientation, broad-tepalled form, and deep, non-fading orange to orange-red coloration. The flowers are borne on an elongate racemose inflorescence with an exceptionally large bud count and with occasional secondary buds (on the lower buds). In addition, the clone possesses to high degree desirable characteristics of hybrid vigor. The clone is a good grower and propagator, as observed at't Zandt, the Netherlands.

My new variety of lily plant has been asexually reproduced by me and under my direction at't Zandt, the Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawings, which show the open bloom in full color and illustrate the unusually elongate racemose inflorescence with its high bud count, its occasional secondary buds, (top photograph) and its dark, slightly ascending pedicels, and in particular the novel and distinctive non-fading deep orange to orange-red outfacing to semi-upfacing flowers (bottom photograph).

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to The Colour Chart of the Royal Horticultural Society, published by the Society in 1966.

The Plant

Origin: Seedling.

*Seed parent.*—Lilium 'Matchless' (U.S. Plant Pat. No. 4,879).

*Pollen parent.*—Unnamed outfacing red Asiatic seedling produced from 'Chinook'×'Burgundy'.

Commercial classification: Hybrid *Lilium* clone.

Horticultural classification: Division I-B, Upfacing Asiatic Hybrid Lily, according to the Horticultural Classification of Lilies, Royal Horticultural Society of London.

Form: Single stem, erect and stately.

Height: 1.25 to 1.75 m from bulbs 12 to 16 cm in circumference, provided their light levels are adequate; low light levels may cause "stretching."

Growth: Vigorous and upright.

Foliage quantity: Abundant.

Size of leaf: 7 to 12 cm long, 2 to 4 cm wide.

Shape of leaf: Lanceolate (pointed).

Texture: Leathery and glossy.

Color: Very dark green, lighter on lower side.

Bulb size: Any size, ranging to 25 cm circumference commercially.

Bulb color: White, with flushes of pink or yellow after exposure to light.

The Bud

Form: Obtuse, ovoid and long.

Size: 7 to 10 cm long and 7 to 12 cm in circumference just prior to opening.

Opening: Bud opens slowly, in response to morning light; this takes about one hour.

Color: Deep orange, R.H.S. C.C. Orange-red 34 D just prior to opening.

Peduncle: Averages 5 to 10 cm, but it may elongate if light levels are too low, if bulbs have been improperly stored prior to forcing, or if bulbs are very large, producing an unusually large inflorescence. Color is deep plum over green, appearing almost black to the eye.

The Flower

Blooming habit: Annually in midseason; flowers once and profusely.

Size: Flowers are large, averaging 12 to 17 cm in diameter, recurving only slightly at the tips on the second or third day to 12 to 16 cm in diameter. Inner tepals average 2.5 to 3 cm wide; outer tepals average 2.25 to 2.75 cm wide.

Borne: In a single racemic inflorescence producing 8 to 20 flowers from a bulb 12 to 16 cm in circumference.

Shape: Broad-tepalled and recurving only very slightly at the tips, creating a "flat face."

Tepalage: Typical of genus *Lilium,* with 6 imbricated tepals.

Tepal color: Deep, non-fading orange to orange-red, basically RHS CC Orange-Red 34 A-B, with color most intense along tepal margins and tips, shading to R.H.S. C.C. Orange-Red 31 B-C just above the nectaries at the midrib of each tepal.

Tepal spotting: Flowers are virtually spotless; they occasionally bear inconspicuous small deep magenta-red papillae at the tepal bases.

Tepal longevity: Tepals stay on stems about four weeks.

Nectaries: Nectaries are generally deep to medium orange, inconspicuous, and lightly pubescent, with short white to orange hairs noticeable only when the flower is completely open.

Pedicel length: Average 7 to 12 cm long, slightly ascending. Lower pedicels generally have secondary buds with pedicels 4 to 6 cm long.

Pedicel color: Dark green with deep plum overlay; appear almost black to the eye.

Pedicel form: Sturdy and ascending, exceptionally strong. Color changes: Flowers become slightly more purple-red as flower ages or when temperatures are very cool.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus *Lilium.* Six stamens with soft orange (R.H.S. C.C. Orange 29 B) filaments 8–10 cm long.

Pollen and anthers (dehisced): R.H.S. C.C. Greyed-Orange 170A to 171B).

Pistil: One in number, soft orange (R.H.S. C.C. Orange 29 A), 6 to 8 long

Stigma: Soft orange (R.H.S. C.C. Orange 29 A to Orange-Red 31 B), medium in size.

Characteristics of ovary: Characteristic of genus *Lilum.*

The Fruit

Fertility: The fruit bears a fertile seed.

Shape: Ovoid.

Color at maturity: Soft brown, overlaid with soft plum.

My new variety of Asiatic hybrid lily most nearly resembles 'Matchless' (U.S. Plant Pat. No. 4,879); but it is taller, with a higher bud count, a much more elongate racemose inflorescence. and with much darker stems and pedicels. Its flowers are slightly smaller than those of 'Matchless,' have a starrier form, and are outfacing to semi-upfacing.

I claim:

1. A new and distinctive variety of Asiatic hybrid lily plant substantially as herein shown and described, characterized by its high resistance to disease, its tolerance of virus, its vigorous growth and rapid natural propagation; the excellence of its flower form and substance; its versatility both as a garden plant and as a cut-flower produced from pre-cooled bulbs forced under glass out of season; and in particular by its unique outfacing to semi-upfacing, non-fading, deep orange to orange-red flowers, borne on an elongae racemose inflorescence with occasional secondary buds, a combination unique among hybrid lilies suited to forcing and to mass commercial cultivation.

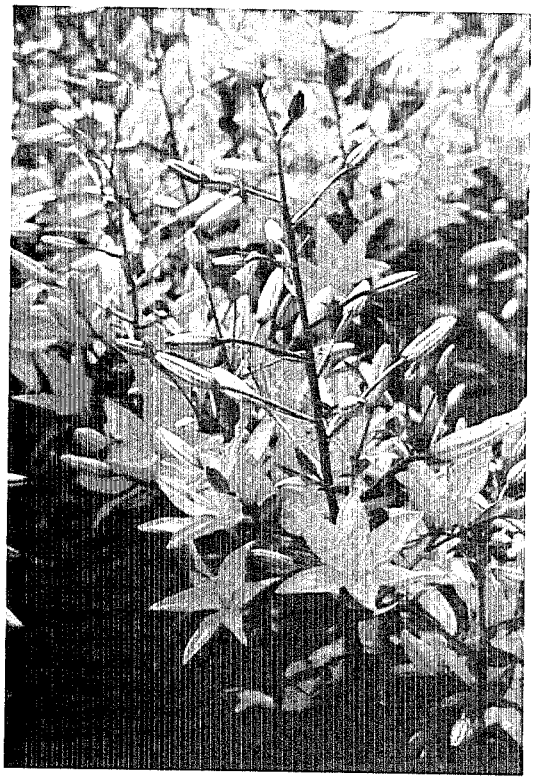
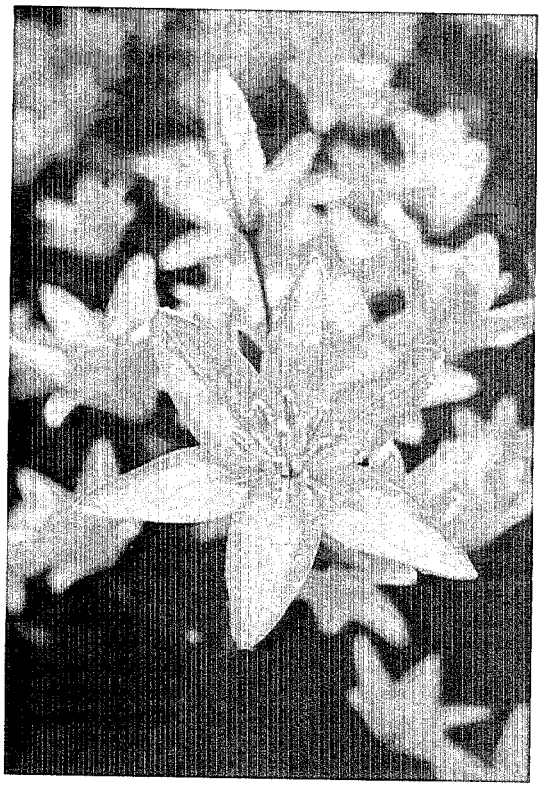

* * * * *